(12) United States Patent
Engelhardt et al.

(10) Patent No.: US 6,263,234 B1
(45) Date of Patent: Jul. 17, 2001

(54) CONFOCAL SURFACE-MEASURING DEVICE

(75) Inventors: Johann Engelhardt, Bad Schonborn; Thomas Zapf, Speyer, both of (DE)

(73) Assignee: Leica Microsystems Heidelberg GmbH, Mannheim (DE)

( * ) Notice: Subject to any disclaimer, the term of this patent is extended or adjusted under 35 U.S.C. 154(b) by 0 days.

(21) Appl. No.: 09/147,995

(22) PCT Filed: Sep. 30, 1997

(86) PCT No.: PCT/DE97/02240

§ 371 Date: Mar. 24, 1999

§ 102(e) Date: Mar. 24, 1999

(87) PCT Pub. No.: WO98/14132

PCT Pub. Date: Apr. 9, 1998

(30) Foreign Application Priority Data

Oct. 1, 1996 (DE) .............................................. 196 40 495

(51) Int. Cl.[7] ....................................................... A61B 6/00
(52) U.S. Cl. ...................... 600/476; 250/559.22; 356/376
(58) Field of Search .................................. 600/473, 476, 600/478; 356/345, 369, 376; 250/559.22, 559.4, 216

(56) References Cited

U.S. PATENT DOCUMENTS

| | | |
|---|---|---|
| 3,812,505 | 5/1974 | Elliott . |
| 4,638,800 | 1/1987 | Michel . |
| 5,383,467 * | 1/1995 | Auer et al. . |
| 5,582,171 * | 12/1996 | Chornenky et al. . |
| 5,601,087 * | 2/1997 | Gunderson et al. . |
| 5,785,704 * | 7/1998 | Bille et al. .............................. 606/17 |
| 5,804,813 * | 9/1998 | Wang et al. ....................... 250/201.3 |
| 6,002,480 * | 12/1999 | Izatt et al. ............................. 356/345 |
| 6,035,229 * | 3/2000 | Lemelson .............................. 600/408 |
| 6,058,323 * | 5/2000 | Silverstein et al. .................. 600/473 |
| 6,069,698 * | 5/2000 | Ozawa et al. ........................ 356/345 |
| 6,095,982 * | 8/2000 | Richards-Kortum et al. ....... 600/476 |
| 6,129,667 * | 10/2000 | Dumoulin et al. ................... 600/424 |
| 6,134,003 * | 10/2000 | Tearney et al. ...................... 356/345 |
| 6,141,577 * | 10/2000 | Rolland et al. ...................... 600/407 |
| 6,150,666 * | 11/2000 | Engelhardt et al. ............. 250/559.33 |

FOREIGN PATENT DOCUMENTS

| | | |
|---|---|---|
| WO 91/03988 | 4/1991 | (WO) . |
| WO 95/25460 | 9/1995 | (WO) . |

OTHER PUBLICATIONS

The Confocal System: Leica TCS NT, product brochure published Jul. 1998.

* cited by examiner

Primary Examiner—Marvin M. Lateef
Assistant Examiner—Shawna J Shaw
(74) Attorney, Agent, or Firm—Simpson, Simpson & Snyder, L.L.P.

(57) ABSTRACT

The invention concerns a device for the confocal measuring of surfaces inside cavities of the body, specially to measure the surface profile (1) of teeth (2) in the mouth cavity. Said device has a probe (3) that can be introduced into the cavity of the body, a light source feeding the probe (3), a detector picking up a light signal (5) and a processor (6) to digitalize the detected signal transforming it into a tridimensional representation. The device is designed using a simple construction and enabling an error free scanning of the surfaces. To this end, the probe (3) is designed as a rotary scanner having at least one deviating device (7) deflecting the light beam (9) in the direction of the surface that is to be measured (1), the deviating device (7) can be positioned in another scanning axis (10) to forward the rotating light beam (9), and the detector (5) comprises a device for sequential or simultaneous scanning of several focal planes, both with regards to specular reflection and to weak scattered light or fluorescent light of the focal plane concerned.

44 Claims, 4 Drawing Sheets

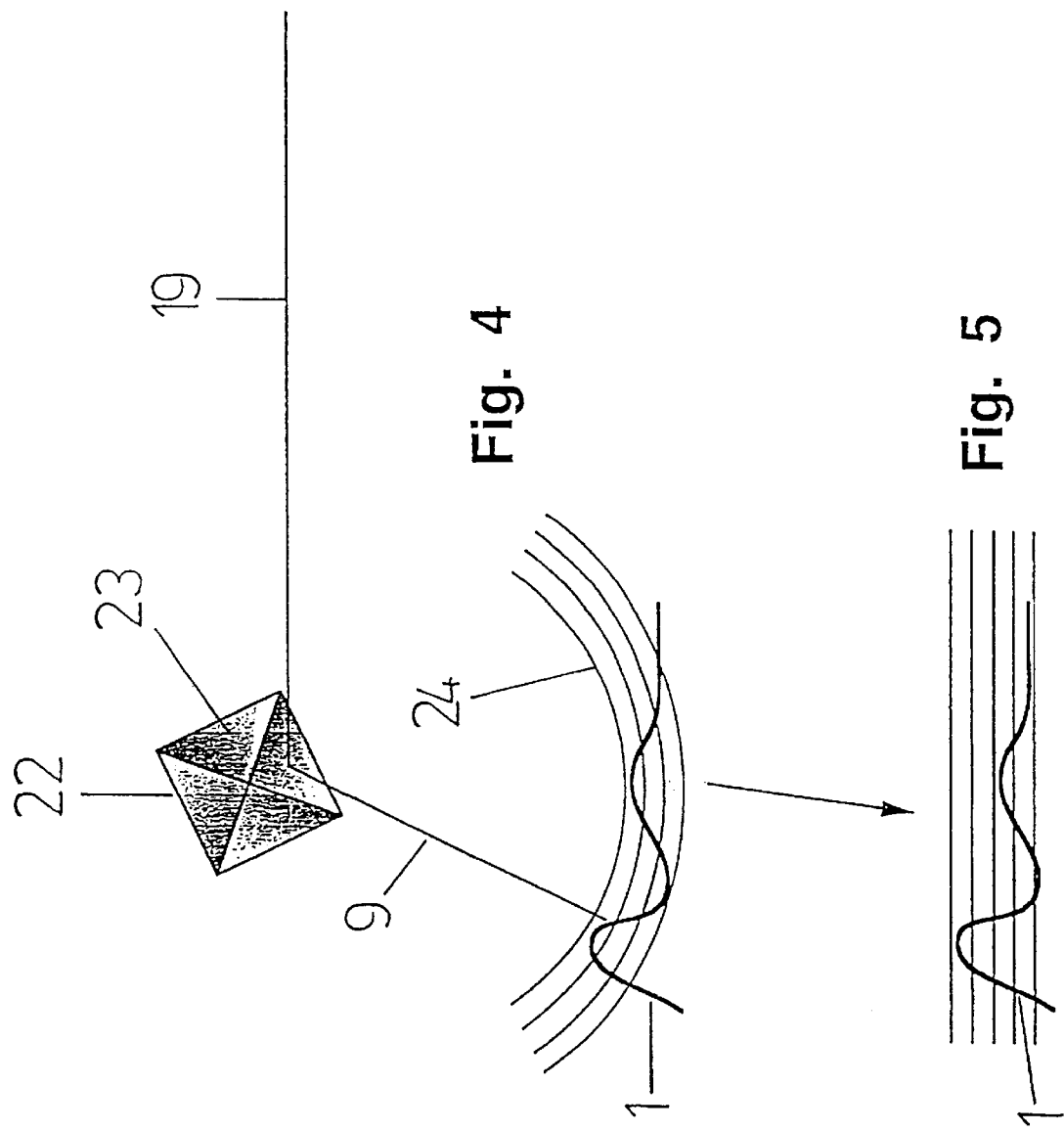

CONFOCAL SURFACE-MEASURING DEVICE

BACKGROUND OF THE INVENTION

The invention concerns a device for confocal surface measurement in body cavities, especially for measuring the surface profile of teeth in the oral cavity, with a probe which can be introduced into the body cavity, a light source supplying the probe, a detector which collects a light signal, and a processor which digitizes the detected signal and processes it.

The invention is based on a method for measuring surfaces of any type or contour. Various processes for surface measurement are known in practice.

For example, a light sectioning sensor can project a line of light onto the object and observe it at an angle using a CCD camera. The geometric deformation of the line is measured. The height differences on the object can be computed from this deformation. By moving the object under the sensor—perpendicularly to the light line—and by repeated measurement of a profile, surface form can be measured or determined from a series of profiles.

The light sectioning sensor is indeed a simply designed and robust sensor, but the oblique lighting which it requires causes unilateral shading of steep surfaces. That causes asymmetries in the imaging, or inaccuracies. Furthermore, error can be introduced into the measurements because of scattering of light from various depths of, for instance, an at least partially transparent tooth material.

Also, a system is already known for measuring the surface profile of teeth in the oral cavity. This means consists of the principal components camera, monitor, and computer. This system is connected directly to a grinding system to produce an inlay. (See Dr. Klaus J. Wiedhahn in DENTAL MAGAZIN 1/95, "Cerec 2—a new epoch?".) For the known system for measuring the surface profile of teeth, the camera or probe is designed so that infrared light is passed though an oscillating grooved grating, and is then reflected from the tooth surface, which is coated with the white powder, $TiO_2$. Then the light passes through a symmetric ray path to the CCD sensor in the camera. Four individual photographs are made at different grating angles in each sequence of photographs (0.2 second). The four individual images are computed to produce a three-dimensional image of the tooth. The three-dimensional "optical impression" obtained with the camera is presented on a high-resolution color monitor as a pseudoplastic image, and the image and structural data are processed in the image-processing computer and the built-in processors, and sent to the grinding unit.

The known process discussed here, and its hardware, have problems due to the fact that it is always necessary to coat the tooth surface with one or more powders to assure a distinct reflection at the tooth surface. Furthermore, the construction of the camera with its CCD sensor is expensive.

Finally, it is already known in practice that surfaces can be scanned with confocal microscopy so as to generate three-dimensional pictures of the surface. In this respect, it is only necessary to refer to Johann Engelhardt and Werner Knebel, "Konfokale Laserscanning-Mikroskopie" [Confocal Laser Scanning Microscopy] in 'Physik in unserer Zeit', Vol. 24, No. 2, 1993, and to D. K. Hamilton and T. Wilson, "Three-dimensional Surface Measurement Using the Confocal Scanning Microscope" in Applied Physics, B27, 211–213, 1982. With respect to a corresponding system—Leica TCS NT—we refer to the Leica brochure "The Confocal System, Leica TCS NT", where application in the dental area is mentioned, particularly on page 16. However, such a system is too large for use in a patient's oral cavity, and too costly to build, and thus too expensive in the confines of dental use.

If we ignore the disadvantages mentioned above, confocal microscopy is very specially suited to surface measurement of tooth surfaces, because this process images only those structures which are exactly in the focal plane of the microscope objective. Thus measurement errors due to the partially transparent tooth material are effectively avoided. To be sure, the method of reflection measurement with the usual confocal microscope fails at steep transitions or flanks if their angle is greater than the aperture angle of the objective, because then the reflection no longer enters the objective, and is lost for evaluation. (See P. C. Cheng and R. G. Summers in Confocal Microscopy Handbook, Chapter 17.)

SUMMARY OF THE INVENTION

Now this invention is based on the objective of presenting a system for confocal surface measurement with which three-dimensional scanning of surfaces in body cavities, such as the surface of a tooth in the oral cavity of a patient, is possible. The probe to be introduced into the oral cavity should be small enough, and simply designed.

The surface measurement system according to the invention achieves the objective stated above by the characteristics of patent claim 1. According to that claim, the system under discussion here for confocal surface measurement in body cavities, especially for measuring the surface profile of teeth in the oral cavity, is designed so that the probe is made in the sense of a rotating scanner with at least one deflecting means. The deflecting means steers the illuminating beam in the direction of the surface to be measured. The deflecting means can be moved along another axis to be scanned to advance the rotating illuminating beam. The detector comprises a system for sequential or simultaneous scanning of several focal planes both with respect to specular reflections and with respect to weak scattered or fluorescent light from the particular focal planes.

It is quite specially significant for the system according to the invention that it is based on the principle of confocal microscopy, and that there is sequential or simultaneous scanning of several focal planes both with respect to specular reflections and with respect to weak scattered light or fluorescent light from the particular focal plane. Now before the very particular design embodiments of the system according to the invention are explained, the fundamental functioning will be discussed in relation to confocal surface measurement and scanning with respect to specular reflections and with respect to weak scattered light or fluorescent light.

Here we are concerned with a system for surface measurement using reflection confocal microscopy, particularly to measure the surface profile of teeth which are being treated or drilled, which is distinguished by confocal imaging with high dynamic response (relative sensitivity) for imaging both specular reflections and also weak scattered light or fluorescent light from the particular focal plane.

With respect to the basic process here, it is known that confocal microscopy of very specially suited for surface measurement of semitransparent materials, as in confocal microscopy only those structures exactly in the focal plane of the microscope objective are imaged. It is also known that the disadvantage of ordinary reflection confocal microscopy, with respect to the aperture problem mentioned above, can be eliminated by utilizing scattered light or fluorescent light from the particular focal plane for the usual evaluation of the reflection.

The confocal imaging can be accomplished highly dynamically, that is, with high relative sensitivity, to carry out an evaluation of the scattered or fluorescent light, so that it is possible both to image highly reflective flat areas and also to show the scattered or fluorescent light even on steep flanks. Accordingly, imaging is possible even if the light reflected from steep flanks misses the objective such that, in the usual reflection process, no profilometry can be done. Finally, the scattered light is always used for evaluation if imaging is no longer possible in the absence of specular reflections by the usual confocal microscopy.

As mentioned earlier, the signal detected is digitized at high resolution, and, as much as possible, at a dynamic range considerably greater than 8 bits. For very effective utilization of the weak scattered or fluorescent light in the areas with steep surface slopes, the relative sensitivity, or dynamic range, of confocal imaging can be 16 bits. Finally, in this way a great brightness difference can be produced by evaluating scattered light in the regions with steep flanks.

An algorithm is provided to evaluate elevations, or to produce the surface profile, using weak scattered light. It takes into consideration, or tolerates, the high dynamic range of the system. This algorithm takes the nearest, or indirectly adjacent focal planes into consideration by interpolating, with the higher intensities in the local region being relatively over-weighted so as to reduce the dependence on the background signals. Finally, a suitable algorithm is provided, so that, after detection of the scattered light signal and after high-resolution digitizing, an adequate height evaluation can be made from the digitized signal.

It must be emphasized here that the surfaces can also be scanned with a dark-field system. Either a point light source or a light source appropriately diaphragined can be provided.

In the area of application to dentistry, and particularly to producing exactly fitted inlays instead of the usual amalgam fillings, it is very specially advantageous first to scan the surface of the untreated tooth and to store the detected values, preferably digitized and already processed to give the height profile. In the next step the tooth is treated or drilled. Then the treated or drilled tooth is scanned again, again with storage of the values giving the surface profile of the treated tooth. From the difference between the two surface profiles, or from the values across the surface profile, the surface, or the exact measurements, are calculated for the inlay required so as to give optimal occlusion of the treated tooth.

It is highly advantageous, to get particularly high precision in processing the inlay, if the inlay being produced is scanned after an initial processing, and if the further processing is done by means of correction values obtained by a comparison of the actual and desired values. Correction to verify the inlay shape is possible to the extent that, with repetition of this process, high precision is possible in producing the inlay and optimal occlusion is possible. The measures described above also allow consideration of inaccuracies caused by the equipment or the tools, such as tool wear, to be taken into consideration so that optimal fitting of the inlay and thus optimal occlusion are possible even with a tolerance range at the processing station.

It is also possible that, in a subsequent step, the cavity produced in the tooth may be filled with a plastic composition so that, when the patient bites on it, the contact points with the opposing teeth are marked in the plastic mass. Then the surface profile generated in that way is scanned, the measurements obtained with respect to the surface profile are stored, and they are taken into consideration in calculating the surface or dimensions of the inlay to be produced.

Now it is of very special importance with respect to the design of the system according to the invention that the probe is designed as a rotating scanner, specifically, that the illuminating beam scans over the surface being measured, or the tooth, in a rotary manner, so that the "focal plane" being scanned by the rotary movement of the illuminating beam is developed as a segment of a cylinder. Then, in the subsequent data processing, an appropriate transformation of the coordinates of the scanned cylinder segment to a true focal plane is required. That is, a geometric correction is required. This is discussed later.

The probe, which is made as a rotary scanner, comprises a deflecting means with at least one reflective surface, which deflects the illuminating beam toward the surface to be measured. The deflecting means, or the reflective surface, can be moved so as to advance the illuminating beam, which is rotated by the deflecting means, along another axis which is to be scanned, so that the rotating illuminating beam, with simultaneous linear movement of the deflecting means, carries out a spiral movement, or a movement similar to a screw thread.

Now, to be able to scan the entire surface profile, with varying heights, that is, with: differing focal points, in the course of the surface scanning, means is also required for sequential or simultaneous sampling of several focal planes. This means is preferably part of the detector. It is always important in this respect that the object is illuminated or scanned by the illuminating beam over a focus region which can be specified. The light which is reflected back after interaction with the object or with the surface of the object is focused by a collecting optical system into the image field, in which the essentially central portion of the light focused there is deflected in the direction of the detection means in multiple image planes. Without considering an actual embodiment of the means for sequentially or simultaneously sampling multiple image planes, it is always important that such sampling—sequential or simultaneous—is accomplished both for specular reflections and for weak scattered light or fluorescent light.

With respect to an actual embodiment of the means according to the invention, particularly with respect to an actual embodiment of the probe and its internal operation, from the viewpoint of simple design, it is quite particularly advantageous if the deflecting means is made as a simple mirror. This simple mirror can be turned or rotated to deflect the illuminating beam at an appropriate angle to the illuminating beam. The deflecting means could also be designed as a prism or as a polygon with multiple facets to produce multiple beam deflectors. In the case of an embodiment as a polygon with multiple facets, it is possible to attain, by an appropriate arrangement, a system with the minimum linear movement orthogonal to the plane swept out by the rotating illuminating beam. We shall return to that later.

In the actual case, the probe can comprise a housing to be introduced into the oral cavity, with a rotatable rotor making up the deflecting means within the housing. Then the deflecting means is placed in the vicinity of an illumination and detection window of the housing, so that the beam directed toward the object to be scanned can arrive, without interference, at the surface to be scanned, at least in a region established by the illumination and detection window. The reflected detection beams returns appropriately back through the illumination and detection window in the probe, via the deflecting means, to a detector which will be explained later.

An optical system which focuses the illuminating beam parallel with the axis of rotation is inside the rotor. This optical system turns jointly with the rotor, so that a rotationally symmetric embodiment is required, in which the optical system and the deflecting system turn jointly in or on the rotor because of their arrangement.

The rotor is guided, or supported in bearings, within the housing so that it can rotate freely and so that it can be moved linearly, in one particularly advantageous and simple embodiment. A special rotor drive is provided for rotation and linear advance of the rotor, although two independent drives can also be used for the rotation and for the linear advance of the rotor. In a very particularly advantageous embodiment, the rotary movement and the linear advance of the rotor are firmly coupled by the rotor having an external thread which is guided, so that it can rotate, in an internal thread in the housing. In order to be able to scan the surfaces with the minimum separations between scans, the threads are designed as fine threads with very low pitch. Such fine threads then suffice to provide the smallest possible linear advance if the deflecting means is a polygon with multiple facets, so that the interaction between low pitch and the geometric arrangement of the facets can provide a linear advance in the vicinity of about 500 micrometers per scan line.

It is also possible to make the thread as a differential thread with very low rate of advance, so that it is possible to attain an advance in the vicinity of preferably 50 micrometers per scan line. It is possible to insert a further means to increase or reduce the linear advance.

The rotor drive which provides the rotary movement and/or the linear advance is advantageously made part of the housing, acting directly between the housing and the rotor. For instance, this drive could be solidly mounted in the housing and could hold the rotor. In the case of an embodiment of the rotor having an external thread, it could act directly on the external thread in the sense of a spindle drive. Here, again, other drive or force transfer variations can be produced.

The light source used to produce the illuminating beam could be a laser light source, and, in particular, a diode laser. In the illuminating beam path from the light source there can be a beam splitter and a means for controlling the focus or for changing the focal length of the illuminating beam. To the extent that the light source is a polyfocal light source, i.e., a light source with different focal lengths, there is no need for a focus control, so that the system can be simplified. Then it would be appropriate for the light source to be followed only by the beam splitter in the illuminating beam path, and the detector would appropriately be a polyfocal detector.

According to the description above, the probe is defined, from the spatial viewpoint, essentially by the housing. The light can be introduced into the probe advantageously by an optical fiber, and the signal produced by interaction at the surface of the object being scanned is carried out of the probe advantageously by an optical fiber.

It would also be conceivable to integrate other functional units which are outside the housing in the foregoing description into the housing or to place them within the housing. For instance, the light source and/or the beam splitter and/or—if necessary—the focusing control and/or the detector and/or the processor could be arranged within the housing by miniaturizing all the functional units. That, correspondingly, would be a compact system needing only connection to the proper power supply. Within the limits of a simple design of the probe, though, it is reduced to the essential functional units, so that the probe is connected by a fiber optic system with the units performing further processing and also with the light source.

Finally, it must be noted that the processor can also take over several functions, such as control, transformation or geometric correction, and digitizing of the signal, serving to compute the three-dimensional surface profile or for storing the data.

BRIEF DESCRIPTION OF THE DRAWINGS

Now there are various possibilities for applying and developing the teaching of the foregoing invention in an advantageous way. We refer to the claims subordinate to patent claim 1, and to the following explanation of three example embodiments of the invention by means of the drawing. In combination with the explanation of the preferred example embodiments of the invention, the generally preferred embodiments and developments of the teaching will also be explained. The drawing shows:

FIG. 4: a schematic presentation of the sampling of an object after deflection of the illuminating beam at a polygon, where the interaction of the rotating movement and the linear advance of the illuminating beam leads to scanning in segments of a cylinder; and FIG. 5: a schematic presentation of the result of the scanning after transformation or geometric correction.

DETAILED DESCRIPTION OF THE PREFERRED EMBODIMENTS

Figure 1:
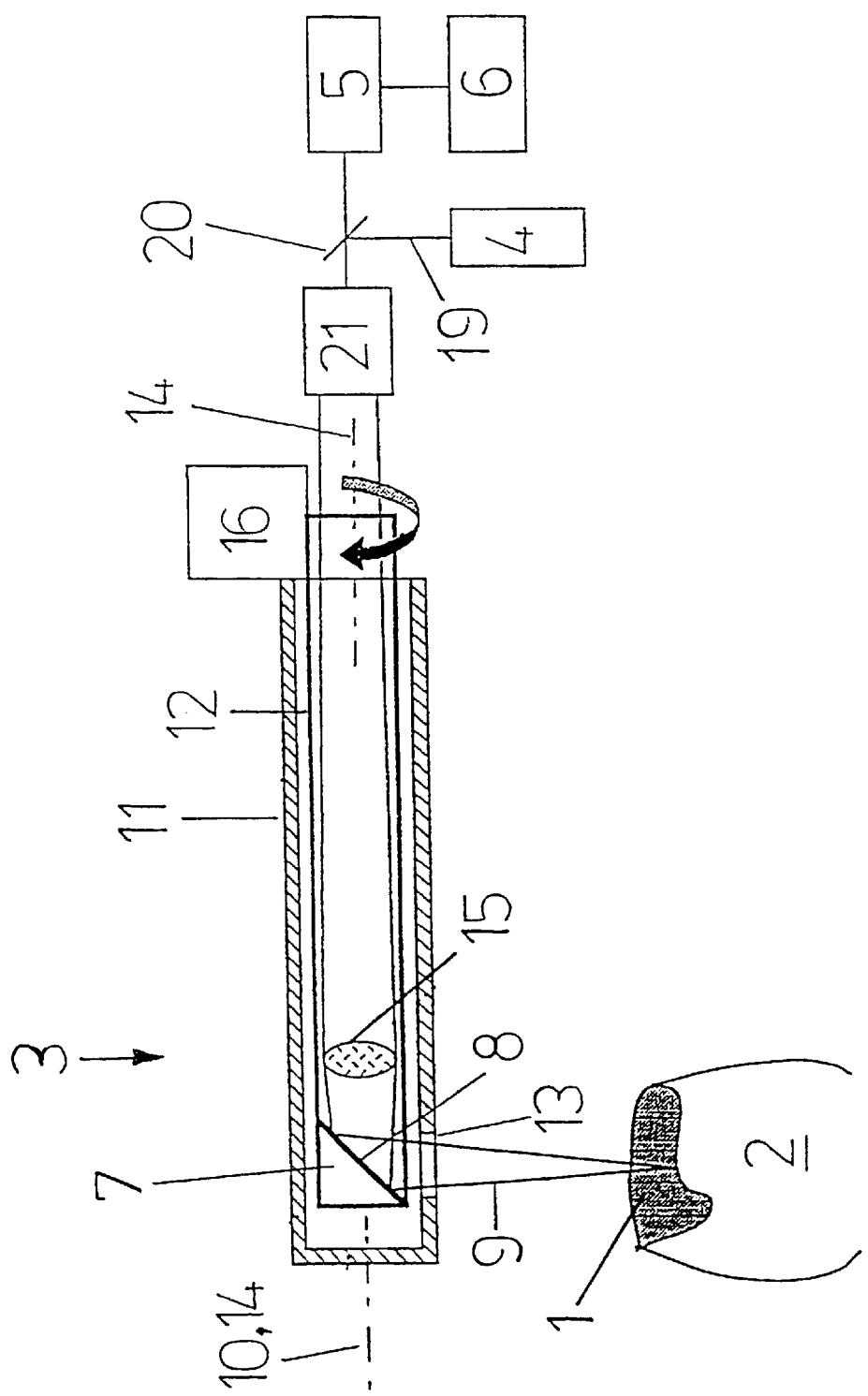
FIG. 1: a schematic presentation of a first example embodiment of the system according to the invention.
Figure 2:
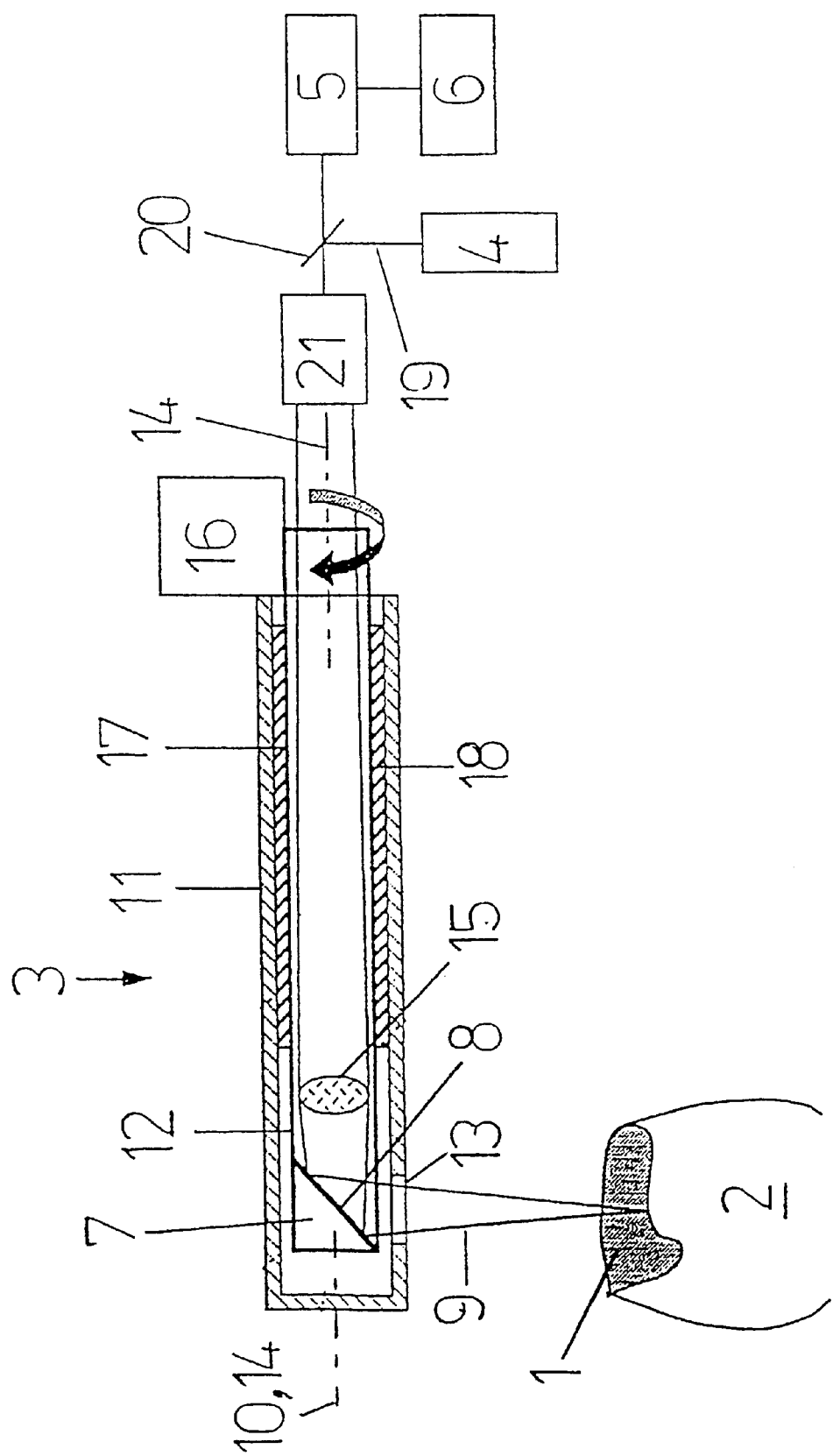
FIG. 2: a schematic presentation of a second example embodiment of the system according to the invention.
Figure 3:
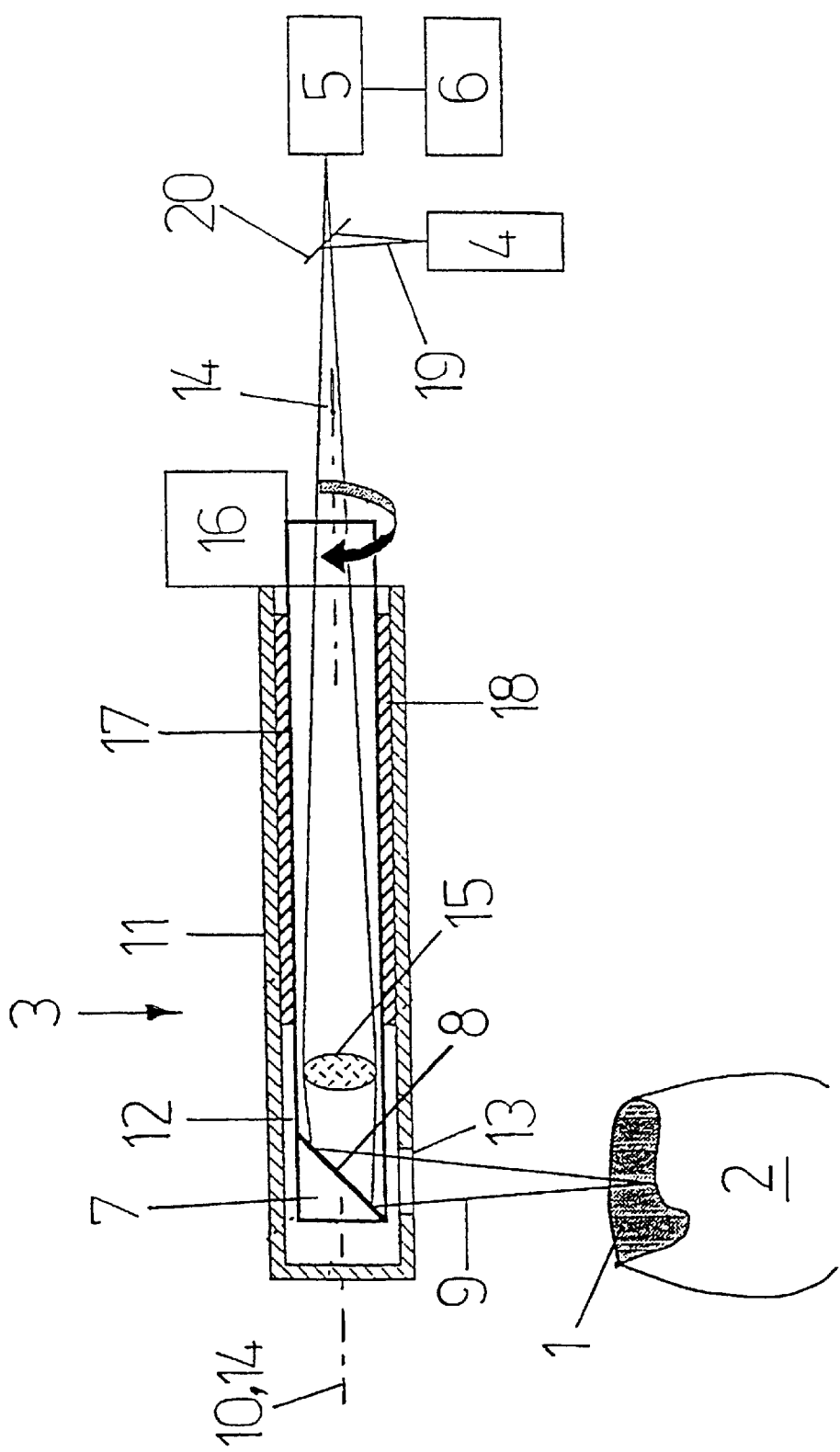
FIG. 3: a schematic presentation of a third example embodiment of the system according to the invention.

FIGS. 1 to 3 show three different example embodiments of a system according to the invention for confocal surface measurement of the surface profile 1 of teeth 2 in an oral cavity not shown here.

The system comprises a probe 3 which can be introduced into the oral cavity, a light source 4 which supplies the probe 3, a detector 5 which picks up a light signal, and a processor 6 which digitizes the detected signal and processes it into a three-dimensional representation.

According to the invention, the probe 3 is made in the sense of a rotary scanner, in which the probe 3 includes a deflecting means 7 with a reflective surface 8. The deflecting means 7 deflects the illuminating beam 9 toward the surface 1 which is to be measured, and the deflecting means 7 can be moved so as to advance the rotating illuminating beam 9 along the scanning axis 10.

The detector 5 has a means, not shown in the figures, for sequential or simultaneous sampling of several focal planes for both spicular reflections or weak scattered light or fluorescent light from the particular focal plane, so that the entire sample or the tooth 2 can be sampled three-dimensionally.

According to the representation in FIGS. 1, 2, and 3, the deflecting means 7 is made as a simple mirror with a single reflective surface 8. With respect to further possible embodiments, we refer to the general description to avoid repetitions.

It is a common feature of the example embodiments shown in FIGS. 1 to 3 that the probe 3 has a housing 11 with a rotor 12 carrying the deflecting means 7 in the housing 11. The deflecting means 7 or the reflective area 8 is placed in the vicinity of an illumination and detection window 13 of the housing 11.

An optical system 15 to focus the illuminating beam 9 which runs parallel with the axis of rotation 14 is placed within the rotor 12.

In the first example embodiment shown in FIG. 1, the rotor 12 is guided or mounted in bearings so that it can be turned freely and advanced linearly within housing 11. A common rotor drive 16 is provided for both the rotary motion and the linear advance of rotor 12. This drive can act on rotor 12 through a special coupling mechanism.

In the example embodiments shown in FIGS. 2 and 3, the rotor 12 has an external thread 17 by which it is guided, so that it can rotate, in an internal thread 18 of housing 11. Thus the rotary motion of rotor 12 is firmly coupled with its linear advance. Threads 17, 18 are designed as fine threads with low pitch, so that just one rotor drive 16 is provided to turn the rotor and thus, necessarily, to produce the linear advance of rotor 12. In all the example embodiments shown here the rotor drive 16 is applied directly to housing 11, so that the rotor drive 16 acts directly between the housing 11 and the rotor 12.

In the example embodiments shown in FIGS. 1 and 2, the light source 4 is designed as a laser light source. Correspondingly, light source 4 is followed in the illuminating light path 19 by a beam splitter 20 and a means 21 for controlling the focus or changing the focal length.

In the example embodiment shown in FIG. 3 the light source 4 is a polyfocal light source. Here only one beam splitter 20 follows the light source 4 in the illumination beam path 19, so that detector 5 is a polyfocal detector. Here, no means is required for focus control or changing the focal length.

In the example embodiments shown in the figures, the light is fed into probe 3 and the light is directed out of probe 3 through a optical fiber not shown in the figures. It acts as a flexible connection between the probe 3 and the light source 4, and also to the evaluation unit, thus serving to take out the signal resulting from the interaction of the light at the surface of the tooth 2 being scanned.

FIGS. 4 and 5 show a schematic representation of the scanning process with a rotating light beam and linear advance. In this case, a polygon 22 is used as the deflecting means 7. The illuminating beam 9 is reflected at a facet 23 of the polygon 22, going from there to the surface profile 1 of the tooth 2. The surface profile 1 is scanned along the cylinder segment 24, one cylinder segment after another, so that different focal planes show the individual focal planes through sequential or simultaneous sampling and with respect to specular reflections as well as with respect to weak scattered light or fluorescent light from the various focal planes.

The scanning values based on cylinder segments are transformed, in a geometric correction, to a "true" focal plane, according to the schematic representation of FIG. 5, so that an undistorted three-dimensional representation of the surface profile 1 or of the tooth 2 can be computed from the scans.

Finally, it must be noted that the example embodiments explained above are intended only to clarify the teaching claimed here by actual cases, but the teaching is not limited to the example embodiments.

LIST OF REFERENCE NUMBERS

1 Surface profile, surface
2 Tooth
3 Probe
4 Light source
5 Detector
6 Processor
7 Deflecting means
8 Reflective surface
9 Illuminating beam
10 Axis (for linear movement of the rotor)
11 Housing
12 Rotor
13 Illumination and detection window
14 Axis of rotation (of the rotor)
15 Optical system
16 Rotor drive
17 External thread (of the rotor)
18 Internal thread (of the housing)
19 Illuminating beam path
20 Beam splitter
21 Means for focus control
22 Polygon
23 Facet (of the polygon)
24 Cylindrical segment (of the scan)

What is claimed is:

1. A device for confocal surface measurement in body cavities comprising:

a light source for providing an illuminating beam traveling along an illuminating beam path;

a probe that can be introduced into said body cavity, said probe being connected to said light source to receive said illuminating beam;

a light-deflecting means carried by said probe for deflecting said illuminating beam in the direction of a surface to be measured;

means for rotating said light-deflecting means about an axis of rotation to generate a profile scan of said surface;

means for linearly advancing said light deflecting means along a scanning axis extending parallel to said axis of rotation to provide a plurality of said profile scans along said scanning axis, said plurality of profile scans corresponding to a focal plane of said illuminating beam;

means for changing the focus of said illuminating beam to scan said surface at a plurality of different focal planes;

a detector for receiving specular reflections of said illuminating beam, weak scattered light and fluorescent light from said surface and generating a sampling signal having information from said plurality of profile scans for each of said plurality of focal planes; and processing means for digitizing said sampling signal and converting said digitized information into a three-dimensional digital representation of said surface.

2. The device according to claim 1, wherein said light-deflecting means is a mirror.

3. The device according to claim 1, wherein said light-deflecting means is a prism.

4. The device according to claim 1, wherein said light-deflecting means is a polygon having a plurality of facets to provide multiple beam deflectors.

5. The device according to claim 1, wherein said probe comprises a housing having an illumination and detection window and a rotor mounted in said housing for rotation about said axis of rotation, and said light-deflecting means is held by said rotor near said illumination and detection window.

6. The device according to claim 5, wherein said illuminating beam travels through said rotor along said illuminating beam path extending parallel to said axis of rotation, and a focusing optical system is placed in said illuminating beam path inside said rotor.

7. The device according to claim 6, wherein said rotor includes an external thread and said housing includes an internal thread mated with said external thread, whereby rotation of said rotor is accompanied by corresponding linear motion of said rotor along said scanning axis.

8. The device according to claim 7, wherein said mating threads are fine threads having a low pitch.

9. The device according to claim 7, wherein said mating threads are differential threads having a very low rate of advance.

10. The device according to claim 9, wherein said rate of advance is approximately 50 micrometers per scan line.

11. The device according to claim 5, wherein said rotor is mounted in said housing for linear motion along a scanning axis, and a rotor drive is connected to said rotor for effecting rotation and linear motion of said rotor.

12. The device according to claim 11, wherein said rotor drive includes two independent drives for effecting said rotation and said linear motion, respectively.

13. The device according to claim 11, wherein said rotor drive is directly attached to said housing.

14. The device according to claim 5, wherein said light source is placed within said housing.

15. The device according to claim 5, wherein said light source is followed in said illuminating beam path by a beam splitter and means for controlling the focal length of said illuminating beam.

16. The device according to claim 15, wherein said beam splitter is placed within said housing.

17. The device according to claim 15, wherein said means for controlling focal length is placed within said housing.

18. The device according to claim 15, wherein said light source, said beam splitter, said means for controlling focal length, said detector, and said processing means are placed within said housing.

19. The device according to claim 5, wherein said detector is placed within said housing.

20. The device according to claim 5, wherein said processing means is placed within said housing.

21. The device according to claim 1, wherein said light source is a laser light source.

22. The device according to claim 21, wherein said laser light source is a diode laser.

23. The device according to claim 1, wherein said light source is followed in said illuminating beam path by a beam splitter and means for controlling the focal length of said illuminating beam.

24. The device according to claim 1, further comprising an optical fiber for transmitting said illuminating beam to said probe and transmitting said specular reflections, said weak scattered light and said fluorescent light from said probe.

25. The device according to claim 1, wherein said processing means controls scanning of said surface, performs a geometric correction from said cylinder segments to true focal planes, and stores said three-dimensional digital representation of said surface.

26. A device for confocal surface measurement in body cavities comprising:

a polyfocal light source for providing a polyfocal illuminating beam traveling along an illuminating beam path;

a probe that can be introduced into said body cavity, said probe being connected to said light source to receive said polyfocal illuminating beam;

a light-deflecting means carried by said probe for deflecting said polyfocal illuminating beam in the direction of a surface to be measured;

means for rotating said light-deflecting means about an axis of rotation to generate a plurality of profile scans respectively corresponding to a plurality of focal planes of said polyfocal illuminating beam;

means for linearly advancing said light deflecting means along a scanning axis extending parallel to said axis of rotation to provide a plurality of said profile scans along said scanning axis for each of said plurality of focal planes;

a polyfocal detector for receiving specular reflections of said polyfocal illuminating beam, weak scattered light and fluorescent light from said surface and generating a sampling signal having information from said plurality of profile scans for each of said plurality of focal planes; and processing means for digitizing said sampling signal and converting said digitized information into a three-dimensional digital representation of said surface.

27. The device according to claim 26, wherein said light-deflecting means is a mirror.

28. The device according to claim 26, wherein said light-deflecting means is a prism.

29. The device according to claim 26, wherein said light-deflecting means is a polygon having a plurality of facets to provide multiple beam deflectors.

30. The device according to claim 26, wherein said probe comprises a housing having an illumination and detection window and a rotor mounted in said housing for rotation about said axis of rotation, and said light-deflecting means is held by said rotor near said illumination and detection window.

31. The device according to claim 30, wherein said illuminating beam travels through said rotor along said illuminating beam path extending parallel to said axis of rotation, and a focusing optical system is placed in said illuminating beam path inside said rotor.

32. The device according to claim 31, wherein said rotor includes an external thread and said housing includes an internal thread mated with said external thread, whereby rotation of said rotor is accompanied by corresponding linear motion of said rotor along said scanning axis.

33. The device according to claim 32, wherein said mating threads are fine threads having a low pitch.

34. The device according to claim 32, wherein said mating threads are differential threads having a very low rate of advance.

35. The device according to claim 34, wherein said rate of advance is approximately 50 micrometers per scan line.

36. The device according to claim 30, wherein said rotor is mounted in said housing for linear motion along a scanning axis, and a rotor drive is connected to said rotor for effecting rotation and linear motion of said rotor.

37. The device according to claim 36, wherein said rotor drive includes two independent drives for effecting said rotation and said linear motion, respectively.

38. The device according to claim 36, wherein said rotor drive is directly attached to said housing.

39. The device according to claim 30, wherein said polyfocal light source is placed within said housing.

40. The device according to claim 30, wherein said polyfocal detector is placed within said housing.

41. The device according to claim 30, wherein said processing means is placed within said housing.

42. The device according to claim 34, wherein said polyfocal light source is followed in said illuminating beam path by a beam splitter.

43. The device according to claim 34, further comprising an optical fiber for transmitting said illuminating beam to said probe and transmitting said specular reflections, said weak scattered light and said fluorescent light from said probe.

44. The device according to claim 26, wherein said processing means controls scanning of said surface, performs a geometric correction from said cylinder segments to true focal planes, and stores said three-dimensional digital representation of said surface.

* * * * *

UNITED STATES PATENT AND TRADEMARK OFFICE
CERTIFICATE OF CORRECTION

PATENT NO.     : 6,263,234 B1
DATED          : July 17, 2001
INVENTOR(S)    : Johann Engelhardt and Thomas Zapf It is certified that error appears in the above-identified patent and that said Letters Patent is hereby corrected as shown below:

<u>Column 11,</u>
Lines 5 and 8, -- claim 34 -- should be deleted, and -- claim 26 -- should be inserted.

Signed and Sealed this

Fifteenth Day of October, 2002

*Attest:*

JAMES E. ROGAN
*Attesting Officer*   *Director of the United States Patent and Trademark Office*